(12) United States Patent
DeMeyer et al.

(10) Patent No.: US 8,065,347 B1
(45) Date of Patent: Nov. 22, 2011

(54) MANAGING PROTOCOL AMENDMENTS IN ELECTRONICALLY RECORDED CLINICAL TRIALS

(75) Inventors: Chris DeMeyer, Lee's Summit, MO (US); Dennis Wijnker, Aliso Viejo, CA (US); Ron Dixon, Santa Ana, CA (US); Hayato Iriumi, Covington, WA (US); Dennis Kochanski, Costa Mesa, CA (US); Nathan Lowe, Cedar Rapids, IA (US)

(73) Assignee: Clinphone PLC

( * ) Notice: Subject to any disclaimer, the term of this patent is extended or adjusted under 35 U.S.C. 154(b) by 236 days.

(21) Appl. No.: 11/963,767

(22) Filed: Dec. 21, 2007

Related U.S. Application Data

(60) Provisional application No. 60/876,230, filed on Dec. 21, 2006.

(51) Int. Cl.
*G06F 17/30* (2006.01)
(52) U.S. Cl. ........................................ 707/806; 707/809
(58) Field of Classification Search .................. 707/806, 707/941, 705, 999.1, 809
See application file for complete search history.

(56) References Cited

U.S. PATENT DOCUMENTS

| | | | |
|---|---|---|---|
| 6,172,068 B1 | 1/2001 | Garvey et al. | |
| 6,173,068 B1* | 1/2001 | Prokoski | 382/115 |
| 6,526,308 B1* | 2/2003 | Heikkinen | 600/436 |
| 6,834,285 B1* | 12/2004 | Boris et al. | 1/1 |
| 2001/0032060 A1* | 10/2001 | Markidan et al. | 702/182 |
| 2002/0029155 A1* | 3/2002 | Hetzel et al. | 705/2 |
| 2004/0243439 A1 | 12/2004 | Huggard et al. | |
| 2004/0249664 A1* | 12/2004 | Broverman et al. | 705/2 |
| 2005/0251011 A1* | 11/2005 | Zahlmann et al. | 600/407 |
| 2006/0224421 A1* | 10/2006 | St. Ores et al. | 705/4 |
| 2007/0061393 A1* | 3/2007 | Moore | 709/201 |
| 2007/0292012 A1* | 12/2007 | Brandon et al. | 382/128 |
| 2008/0154640 A1 | 6/2008 | DeMeyer et al. | |
| 2009/0016579 A1* | 1/2009 | White et al. | 382/128 |

* cited by examiner

*Primary Examiner* — James Trujillo
*Assistant Examiner* — William Spieler
(74) *Attorney, Agent, or Firm* — Wolf, Greenfield & Sacks, P.C.

(57) ABSTRACT

A clinical trial management system and associated methods are provided to manage individual clinical trials running under multiple protocols at once. The disclosure allows clinical trials to be amended during the course of the study with reduced risk of loss of time or data. Patients may be started under one clinical trial protocol and be moved to another upon approval from the doctor or hospital managing their involvement in the study. In an embodiment, patient data is not moved or altered during a change in protocol to provide a more secure clinical trial system.

13 Claims, 4 Drawing Sheets

Metadata Tables

Item Definition

| | Item | Type | CodeList |
|---|---|---|---|
| BDT | 5 | String | Codelist |
| BDT | 6 | Float | Codelist |
| ... | ... | ... | ... |
| BDT | 206 | Integer | Codelist |
| | 6 | | |

Protocol Question Table

| Version | Question | Item |
|---|---|---|
| 1 | 1 | 5 |
| 1 | 2 | 6 |
| ... | ... | ... |
| 2 | 200 | 206 |
| 2 | 210 | 6 |

Protocol Item Table

| Data Item | Protocol | Prot. Item |
|---|---|---|
| ... | ... | ... |
| 5 | 1 | 1 |
| 6 | 1 | 3 |
| 206 | 2 | 1 |
| 6 | 2 | 4 |

Metadata Question Table

| | | |
|---|---|---|
| 1 | Are you over 21 years of age? | |
| 2 | Amount of Pain (1-5 scale) | |
| ... | ... | |
| 200 | What's your age? | |
| 210 | Amount of Pain (1=min, 5=max) | |

FIG. 4B

Actual Data Items

| Pointer | Data |
|---|---|
| 1 | Yes |
| ... | ... |
| 5 | Yes |
| 6 | 4.5 |
| 7 | 68 |
| ... | ... |
| 205 | O- |
| 206 | 25 |
| ... | ... |

FIG. 4A

MANAGING PROTOCOL AMENDMENTS IN ELECTRONICALLY RECORDED CLINICAL TRIALS

CROSS REFERENCE TO RELATED APPLICATIONS

This application claims the benefit of U.S. Provisional Application No. 60/876,230, filed Dec. 21, 2006, entitled "System and Method for Managing Protocol Amendments in Electronically Recorded Clinical Trials." The foregoing application is incorporated in its entirety by reference herein.

BACKGROUND

1. Field of the Disclosure

The present disclosure generally relates to the computer storage and management of clinical trials. In particular, the present disclosure relates to upgrading or altering a particular protocol of a particular clinical trial.

2. Description of the Related Art

Before a new medical treatment (e.g., pharmaceuticals) or device (e.g., surgical instruments or implants) may be dispensed to the public, the United States Food and Drug Administration (FDA) requires that the manufacturers of the pharmaceuticals, devices, instruments, or implants conduct extensive clinical trial research in order to demonstrate the clinical effectiveness, safety, and medical advantage of their products. Extensive and often complex clinical trial protocols are developed that define, for example, targeted demographics, proposed medications, patient regimens, forms for collection, types of statistically relevant data, the timing or order of events within the study, often even the layout of the reporting data, or other suitable data. These protocols are often sufficiently complex that the protocols themselves receive FDA approval.

Once a protocol is developed and approved, companies design electronic data capture and data management solutions to manage the data gathered over the course of the clinical trial. This typically includes configuring a database to store the patient data as well as study metadata. The study metadata generally defines events (and scheduling thereof), Case Report Forms (CRFs), data points and their grouping, code lists, business rules, and derivatives (calculated fields). In general, such data capture and data management solutions capture data from geographically disparate clinicians or study participants, defining many points of data entry, potentially across many software and hardware platforms.

During the course of a clinical trial, one or more protocol amendments may occur, such as when new information becomes available or by request of a sponsor or regulatory agency (e.g. the FDA). Protocol amendments occur for a variety of reasons. Sometimes additional or more specific information is desired; other times a clinical trial is started as early as possible and details are fleshed out along the way. Still other times, protocol amendments merely involve clarification of forms that are used. A protocol amendment often requires a different version of a study, and each participating site (typically each physician's office or hospital) generally needs to receive Institutional Review Board (IRB) approval prior to the deployment of a new version of the study metadata. These approvals take varying amounts of time and it would generally be inefficient, if not impractical, to wait for all approvals before updating the trial protocol. Even when possible to wait for each participating location to approve a protocol change, valuable data may be lost by holding back the early adopters. As such, allowing different sites to utilize different versions of the trial protocol is advantageous.

Most systems that attempt versioning create new databases and import the data from a previous database to the new one. One drawback of this sort of versioning is the potential for data corruption or loss when moving the patient records from one protocol to another. Another drawback is that this sort of versioning may also cause a need for revalidation of the data or the system by the FDA. It is therefore desirable to provide a system and method of protocol versioning which reduces or eliminates the need to move data.

SUMMARY

The present disclosure includes embodiments of systems and methods for providing robust versioning of clinical trial protocols. Providing versioning advantageously allows various participating locations to migrate to newer protocols at their own pace. Additionally, an embodiment of the present disclosure reduces or eliminates the need to move or copy data when amending a protocol thereby advantageously avoiding data loss or corruption.

One aspect of the present disclosure includes a clinical trial management system having a processor capable of accepting clinical trial data, a database capable of storing the clinical trial data, metadata defining a protocol for managing the clinical trial data, and a staging and publishing module capable of accepting additional metadata defining a new protocol. The staging and publishing module may also be capable of adding data elements to the database in accordance with the new protocol without disturbing data entered under the previous protocol, and the processor may also be capable of managing incoming clinical trial data according to the various protocols.

Another aspect of the present disclosure includes a method of managing multiple clinical trial protocols for a single clinical trial, the method including storing metadata defining a first protocol storing data in a database, accepting second metadata defining a second protocol, updating the database to store data according to both the first and second protocols. The method can also include tracking patients' participation in one of the protocols and managing patients under the correct protocol.

Another aspect of the present disclosure includes a method of staging a new clinical trial protocol in a clinical trial that is already underway, the method including retrieving metadata defining a current protocol, accepting second metadata defining a new protocol, comparing the two sets of metadata, and generating a report of the differences.

Yet another aspect of the present disclosure includes a method of migrating patient records from one clinical trial protocol to an amended protocol, where a patient record includes generic data storage and metadata defining and referencing the data storage. The method can also include adding new data elements to the data storage and/or updating references in the metadata to different data elements. Additionally, queries and derivations can be run on the resulting data elements. In an embodiment, none of the steps alter, move, or destroy data utilized.

For purposes of summarizing the disclosure, certain aspects, advantages and novel features of the disclosure have been described herein. Of course, it is to be understood that not necessarily all such aspects, advantages or features will be embodied in any particular embodiment.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit the scope of the disclosure. Throughout the drawings, reference numbers are re-used to indicate correspondence between referenced elements.

FIG. 4A illustrates a simplified exemplary table of data items illustrating features of the disclosure herein.

FIG. 4B illustrates simplified exemplary metadata tables illustrating features of the disclosure herein.

DETAILED DESCRIPTION

Figure 1:
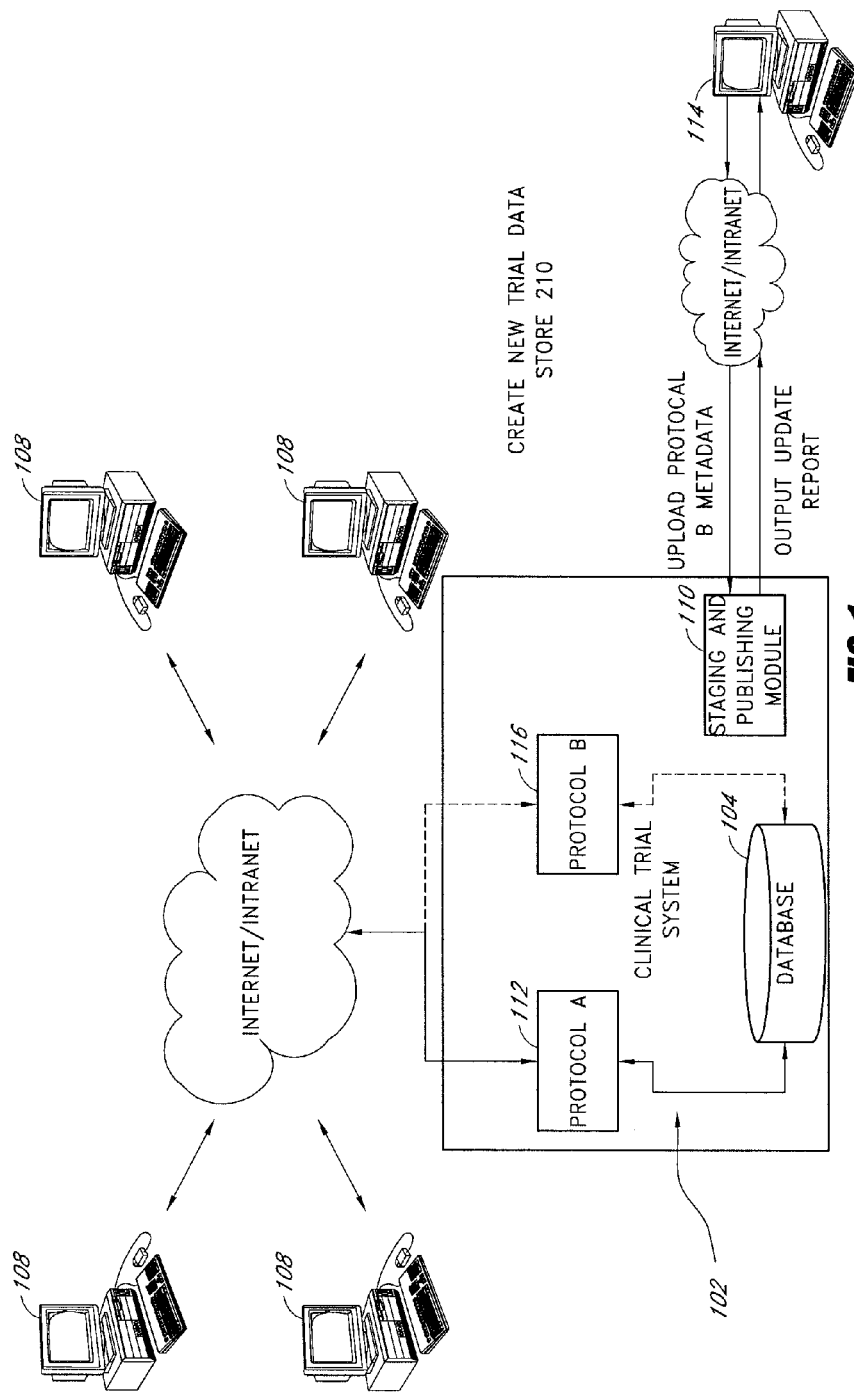
FIG. 1 illustrates an overview of an embodiment of a clinical data study system including an embodiment of a clinical trial system having upgrade features according to the disclosure herein.

In an embodiment, a clinical trial data management system utilizing protocol versioning, comprises a database that is capable of accepting and storing data from at least one clinical trial. The system is further capable of managing more than one trial protocol for a given clinical trial. This management system, in an embodiment, is capable of connecting to distributed users through a communications medium, such as, for example, the Internet, a LAN, a WAN, or other suitable mediums. In an embodiment, users utilize a computing device with a web-based interface to access the clinical trial, for example, to store, edit, and/or retrieve data or the like from the clinical data store. In many cases, users will access the data store through a FDA validated protocol. However, it may be determined that the protocol needs to be changed. In an embodiment, alterations to a protocol are accomplished using a protocol designer tool, such as those tools commercially available from ClinPhone, Plc. of Nottingham, UK. Suitable designer tools have also been described in U.S. application Ser. No. 11/045,789, entitled System and Method for Configuring Electronic Data Capture and Data Management Systems for Clinical Trials, which is assigned to the assignee of the present disclosure, and the entire disclosure of which is incorporated herein by reference.

Once the amended protocol is designed using a designer tool or any other method, one or more files defining the amended protocol may result. In an embodiment, this file or the multiple files are uploaded to the system. In an embodiment, the amended protocol then goes through a staging process. During this process, the amended protocol can be compared to the previous protocol. In an embodiment, this comparison generates a report of all alterations between the earlier and amended protocols. This advantageously helps the designer to confirm that no more or fewer changes than are desired have been made between the two protocol versions.

If the designer approves of all of the alterations made, then the amended protocol will be published. Protocol amendments often must be approved by local IRBs before the study site that the IRB governs can utilize a new protocol. As such, it is preferable to allow access to both protocols once the amended protocol is published. Sites which have not yet received approval may continue under the previous protocol.

On the other hand, once an amended protocol is published, in an embodiment, the doctors, hospitals, and the like who have approved the use of the amended protocol start new patients under the amended protocol. In an embodiment, patients started prior to the protocol amendment continue under the old protocol or are migrated to the amended protocol. Preferably, this migration does not move any data that has been collected for the patient. As will be described in more detail herein, some data may need to be revalidated by a doctor or other system user. If data types for an answer to a form question have changed, for example, in an embodiment, a new data element is created and accessed under the amended protocol. The old data is preferably not moved or deleted, however. In this way, older data is preserved and may be accessed again if needed.

System

Systems and methods representing various embodiments and example methods of carrying out protocol versioning will now be described with reference to the figures. Corresponding numbering indicates corresponding parts, and the leading digit indicates the figure in which an element first appears.

As generally described above, most clinical trials involve gathering data from disparate geographic locations across the country or around the world. As such, a networked computing system is often employed. In many instances, this will take the form of a centralized clinical trial management system 102 including one or more associated databases 104 capable of storing clinical trial data. The management system 102 typically may be connected to a communications medium 106, such as, for example, a WAN, LAN, wired or wireless network, or other suitable mediums. In an embodiment, the communications medium 106 is the Internet or the World Wide Web. Through the communications medium 106, users 108 can access the clinical trial management system 102 to input patient records, retrieve records, manage patients among various protocols and studies and the like. Generally, a user 108 can be a doctor, hospital, clinic, or someone working on their behalf to participate in a given clinical trial. In an embodiment, clinical trial management system 102 includes a web server allowing users 108 to access the clinical trial management system 102 through a personal computer having a standard web browser, such as, for example, Internet Explorer®, FireFox®, Safari®, Netscape Navigator®, or other suitable web browser. In an embodiment, users utilize a web-enabled device, such as a mobile phone, PDA, personal game device, or other suitable device, a general purpose computer utilizing a particular clinical trial application, a dumb terminal, and the like.

The management system includes a staging and publishing module 110 to aide in updating protocol versions. When a clinical trial is initially set up, a first protocol 112 is designed and implemented, possibly utilizing the design tool discussed above. At this point, all patient records are stored in the database through the first protocol 112, and the first protocol 112 will determine what forms appear on a user's screen for input and management of patient data, the format of data, qualifying criteria, and the like. However, a study designer 114 can create a amended protocol 116 which can be created by or loaded to the staging and publishing module 110, which readies and implements the amended protocol 116 for use by users 108. In an embodiment, once the amended protocol 116 is implemented, management system 102 tracks which users and/or which users' patients utilize which protocol and interact with the user 108 appropriately.

EXAMPLES

Before getting into more detail on the workings of the system, it may be instructive to describe examples. These examples will be discussed with reference to FIGS. 4A and 4B. A trial management system as disclosed herein preferably utilizes generic data items for storing data while one or more metadata tables are used to understand and interpret the data items. Utilizing the teachings herein, trial protocols can be changed and data updated without physical movement of the data.

In a first example, the clinical trial is set up with Protocol 1. Among the data collected and stored may be the answer to the question "Are you over 21 years of age?" Perhaps, the study designers initially were only interested in, for example, the differences in effects between children and adults. As can be seen in FIG. 4A, the clinical data store maintains one or more tables or similar records of the actual data to be stored. In an embodiment, each patient record has its own table of generic data items. The data items can be accessed by means of pointers, in an embodiment. In an embodiment having generic data items, metadata is generally stored for interpretation of the data items. Examples of possible metadata tables are shown in FIG. 4B. First, the Item Definition table can be utilized to interpret the data types for each of the actual data items. For example, item 1 is a string, and looking to the actual data items, item one for that patient is "Yes." While it is helpful to understand the data type for data, it is generally more useful if associated with context, such as the question that it answers. As such, in an embodiment, a Metadata Question Table stores form questions and a Protocol Question Table associates those questions with the corresponding data items. For example, Protocol 1 question 1 is "Are you over 21 years of age?," and the associated answer can be found in data item 5, which corresponds to "Yes." In an embodiment, a Protocol Item Table translates an individual protocol's item numbers into actual data items, so that the answer to Protocol 1's question 1 is mapped differently than Protocol 2's question 1.

Returning to the example, the protocol designers may realize several months into the study that they would like more detailed degradations of patients and wish to change the study protocol to ask the question: "What's your age?" In such a case, not only must the question asked be changed on the forms, but the type of data collected will change from a "Yes"/"No" string to an integer value. It is preferable, however, to accomplish this change without losing data.

As can be seen from the figures, the original question is stored in the Metadata Question Table as question 1. The Protocol Question Table shows that Protocol 1's question 1 is answered in actual data item 5. The Item Definition Table defines what type of data each data item contains. From these tables, it can be determined that "Are you over 21 years of age?" is protocol version 1, question 1; its answer is stored in data item 5 and it is a string, which, for the example patient shown here, is "Yes."

When the study designers wish to change the protocol, however, to determine the actual age of each patient, new entries may be added to the tables, such as in the example tables. These updates are shown in the grayed table entries. It is preferable to add new entries so that data is not lost or altered. This is preferable at least because not all patients may be tracked under the same protocol at all times and access to the various versions of questions and stored responses is desirable. Additionally, this type of protocol upgrade may avoid revalidation by the FDA or some other governing entity. In the example shown here, the designers chose to change the first question to "What's your age?" Once the designer finishes the new protocol, he or she will publish the changes. As seen, the original question is preferably not changed, but rather the new question is preferably added at the end of the question table (creating a new question 200). While the answer is still item 1 for the protocol (Protocol Item Table), this is a new protocol, and a new item 206, as can be seen, may be added to the Protocol Item Table. Additionally, the Protocol Question Table is updated with Protocol version 2 showing question 200 is associated with data item 206. The Item Definition Table will also be updated with item 206 being definable as an integer.

In an embodiment, when a patient is transferred over to protocol 2, the new question may be flagged to receive a new answer (as here, looking to item 206, the patient turned out to be 25). This can be referred to as requiring new validation of the data. In an embodiment, all of the questions and data remain so that some patients may be run on protocol 1, while others are run on protocol 2. Additionally, it may be possible to retrieve historical information for a patient that started on protocol 1 and was switched to protocol 2.

In another example, a question may merely be reworded, perhaps to clarify the answer. Original question 2 in protocol version 1 read "Amount of Pain (1-5 scale)" and it was associated with the data item 6. For the patient data shown in the example, the pain was listed as 4.5. While the new protocol 2 may clarify this question, the data itself may not change. In an embodiment, both the old and new question are associated with the same data item 6, and no new data item is created for a simple change. In such an embodiment, patients on the different protocols answer the differently worded question, but the resulting input is stored in the same data element. When a change such as this appears minor, the data may or may not change its validation status based on rules decided by the system or input by the protocol designer.

Methods

Figure 2:
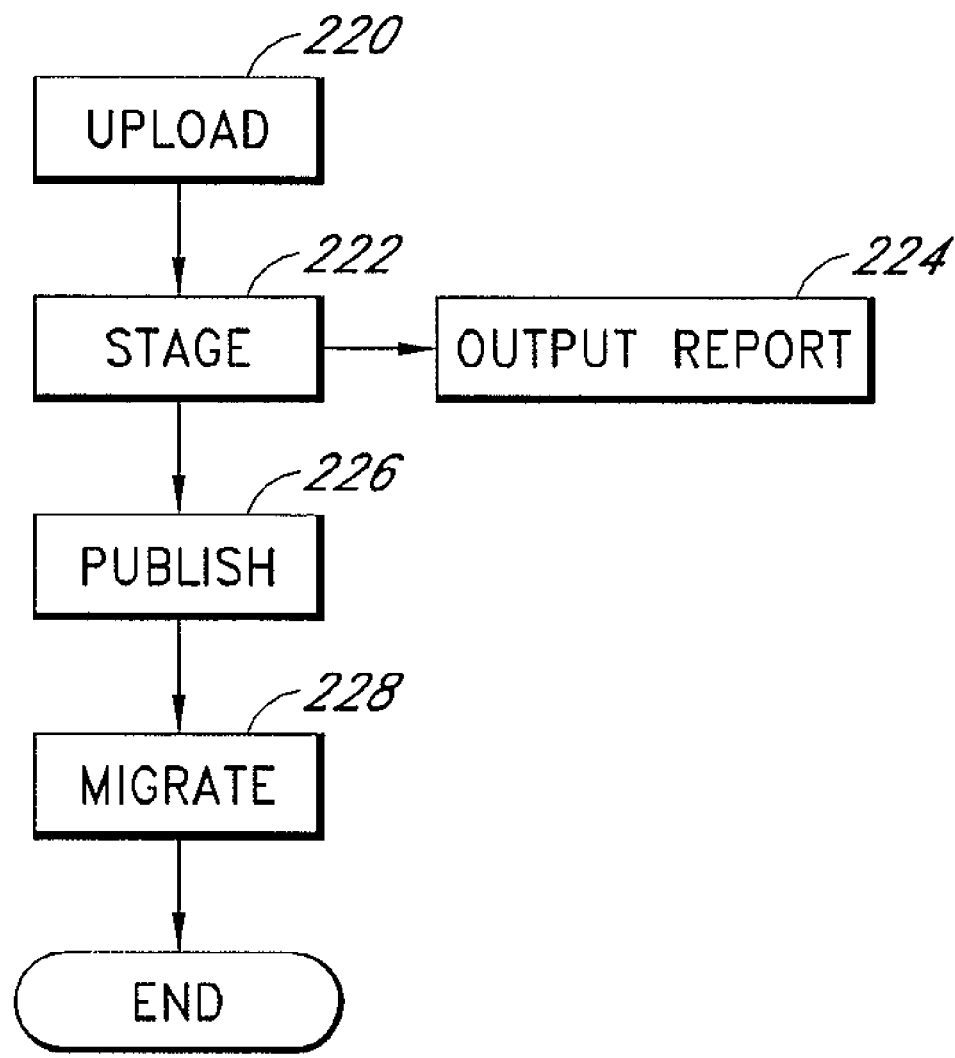
FIG. 2 illustrates a block diagram of an exemplary method of updating a clinical trial study according to the disclosure herein.
Figure 3:
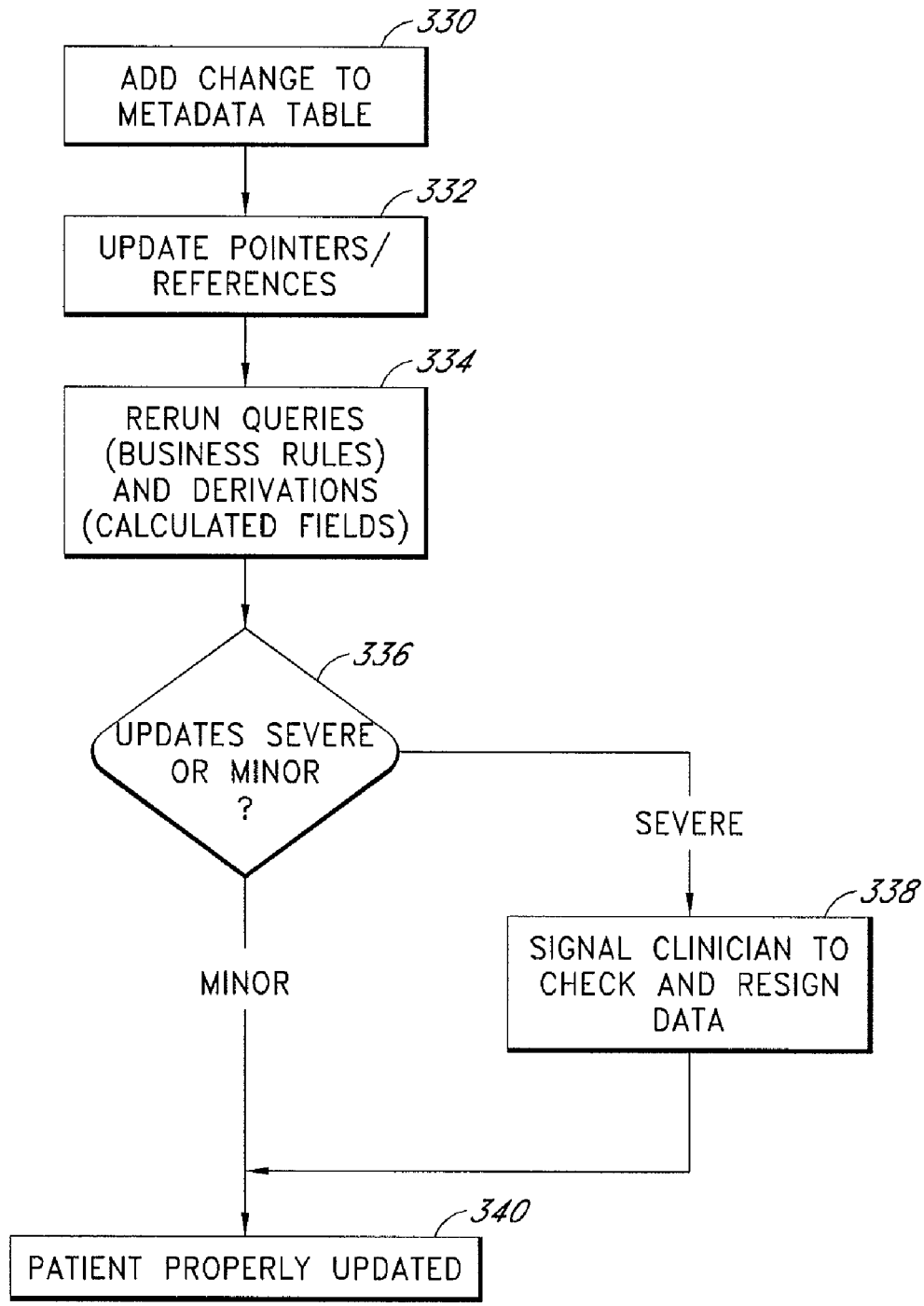
FIG. 3 illustrates a block diagram of an exemplary migration process of the exemplary update process of FIG. 2.

With this understanding of the general make-up and workings of embodiments of the present system, exemplary methods of operating the disclosed systems will be disclosed. Turning to FIGS. 2 and 3, the operation of the clinical trial management system is explained in greater detail. In general, in an embodiment, there are four or five steps in upgrading a protocol. First, the amended protocol is designed, either online if the functionality is provided as a part of the clinical management system 102 or offline, such as on a computer preferably utilizing a designer tool as disclosed above. Once the designer is satisfied with the make-up of the amended trial protocol, at least one new metadata file is created that describes the amended protocol. The one or more metadata files may utilize one or more metadata tables, such as those shown in FIG. 4B. As will be well-understood, metadata tables may be set up differently, two or more of the tables pictured in FIG. 4B can be combined, a pictured table may be split apart, or the like. While it is preferable for metadata file(s) to fully define a protocol, the metadata may also be used to describe deviations from defaults, additions to a basic standard protocol, or the like. In an embodiment, the metadata file comprises one or more xml files.

Turning to FIG. 2, in an embodiment, once a metadata file is created, it is uploaded to the clinical trial management system 102 and the staging and publishing module 110 specifically (block 220). In an embodiment, this new file is then staged (block 222). The staging process compares the metadata files from the current protocol 112 with the newly uploaded metadata file. With this comparison, in an embodiment, a report is generated describing all of the changes that have been made between the two protocols. The report can be output (block 224) to the designer 114. Such a report can allow the designer 114, users 108, or the like to confirm that all changes, and only the exact changes desired, are being made with the amended protocol If the designer 114 does not like the report, in an embodiment, additional changes to the amended protocol and metadata files are made, uploaded (block 220) and restaged (block 222) before proceeding.

Next a metadata file describing the amended protocol is published (block 226). At the publishing stage, the amended protocol 116, described by the metadata file, is instituted. The clinical trial management system 102 can create any newly required data elements and the like in the database 104 and allow users 108 to initiate use of the amended protocol 116 to access and store information in the clinical database 104. At the publishing stage, in an embodiment, there may be an option to migrate all patients in a study over to the amended protocol. This typically will happen in instances of minor changes, such as cosmetic form changes or business logic changes. If the changes are minor, a designer 114 may move all patients to the amended protocol. In an embodiment, this may also trigger a "clean-up" function that removes or hides the original protocol 112 from access by users 108.

Often times changes will be more significant and will require the approval of an IRB before users 108, such as hospitals and clinics, can move patients to an amended protocol 116 or begin use of an amended protocol 116 by new patients. In these instances, individual users 108 may be allowed to initiate migration (block 228) of their patient's individually (or by groups, such as all patients cared for by that user 108) at various times after receiving their own IRB approvals. Whether migration is done en masse as initiated by the designer 114 or is done individually by different users 108, an embodiment of the migration stage is shown in FIG. 3. During migration, in an embodiment, changes to a patient's metadata tables are made (block 330). This may involve, in an embodiment, associating a patient with one or more master metadata tables under the amended protocol 116 or changes to individualized metadata tables. Additionally, in an embodiment, pointers or references to the patient's actual data tables are upgraded (block 332). For example, a protocol question table, as shown in FIG. 4B, can have a question that remains the same, but the response data type change. In that case, the table entry that points or refers to the actual data item can change from the old data item to point to or refer to a new data item. As with any changes according to the present disclosure, the old data item is preferably not altered, deleted, or overwritten. This allows data to be retrieved from old protocols if needed and helps prevent data corruption.

Typically, in a clinical trial, the data entered on a patient must be validated by the user 108 (i.e. the doctor or clinician overseeing the patient's participation in the study). In some instances, protocol amendments will not have any affect on a user's previous validation of data. However, other amendments, while preferably not deleting or altering data under the previous protocol, may still affect some data.

As such, during migration, it is preferable to rerun queries and derivations. Queries refer to business rules while derivations refer to calculated fields (e.g., age, when data requested date of birth and current day is known). In running the queries and derivations, the system will preferably check whether the changes between protocols have been severe or minor (block 336). If the updates are minor, the queries and derivations may be completed unimpeded and the patient migration will be complete. If the changes are more severe, such as if a question and its associated responding data type are changed (e.g., the change in the age question described above and illustrated in FIG. 4B), the user 108 will preferably be alerted (block 338) that additional patient information may need to be entered or that information may need to be verified and validated. In such a case, once a user 108 reviews any flagged data or adds any new data, the user 108 can validate the new data to complete the patient update to the amended protocol 116.

It is preferred that a patient only be associated with one protocol at any one time. In an embodiment, the clinical trials managed by the system are less prone to inconsistent data gathering. In an embodiment, only two protocols are active at any one time. However, the system as disclosed can also be configured to manage any number of protocols for each clinical trial.

System Details

As stated, in an embodiment, the clinical trial management system is connected to distributed computer systems by a communications network 106.

Clinical Trial Management System 102

Clinical trial management system 102 comprises a database 104, a staging and publishing module 110, and one or more protocols 112, 116. In an embodiment, the management system controls multiple clinical trials, each having one or more protocols 112, 116 and one or more databases 104. In an embodiment, the management system 102 comprises a secure web server allowing, for example, users 108, to interact with the management system 102 and its trial database(s) 104 through their own web-enabled devices (e.g. computers, PDAs, internet-enabled phones, etc.). Access may be granted to clinical trial web pages after gaining access through a login and password. The management system 102, in an embodiment, provides web forms for the entry and management of clinical trial data for various participating patients. In an embodiment, the management system 102 and user's 108 systems act as server and clients, such as, for example, with a Java, JavaScript, Jscript, or other suitable programming language-based applet or stand alone application. In an embodiment, data entry occurs at the management system 102 itself.

The management system 102, in an embodiment, serves or accepts HTTP requests or similar requests from users 108 and responds with appropriate html files, active server pages, Java, J-script, applets or other suitable responses. In an embodiment, the management system 102 has separate home or entry pages for each clinical trials being managed. In an alternative embodiment, a single login screen may be utilized for all trials and the entered login and/or password are reviewed by the management system 102, which may alternatively provide a protocol 112, 116 choice for the user 108 or grant access to the clinical database 104 only through one protocol 112, 116. The latter may occur, for example, when a user 108 has migrated all patients to a new protocol 116 or when use of a new protocol has not yet been approved for a user's 108 site.

Management system 102 can be comprised of a single processor or multiple processors working in conjunction, running suitable software capable of performing the required operations. Alternatively, management system 102 can include a circuit board with hard-coded instructions. The management system 102 can also be discerned by one of ordinary skill in the art from the description herein.

Clinical Database 104

The management system also comprises or is linked to clinical database 104, which can include a series of physically disparate databases—such as a networked group of server databases, or databases housed on individual hard drives—or virtual databases, segmented on the same hard drive(s). In an embodiment, each clinical database 104 comprises a database including the data of one or a group of clinical trials. An artisan will understand from the present disclosure that an embodiment of a clinical database 104 includes different data based on the study with which it is associated. Generally, however, data can include a plurality of patient or clinical trial subject entries. Each entry can include such information such as, for example, patient initials, a patient identification number, patient history, drug or treatment dosage information, vitals, observations, side effects, physician notes, or other suitable information. Each patient record can include a table of actual stored data (such as FIG. 4A). In an embodiment, each patient record includes patient-specific metadata tables (such as one or more of the tables in FIG. 4B). It is understood, however, that in an embodiment metadata tables are clinical trial specific and generic as to each participating patient. In an embodiment, any patient data is encrypted to help protect the integrity of the information and lessen unauthorized tampering with it.

Staging and Publishing Module 110

The staging and processing module is preferably a software module implemented by the management system 102 hardware. In an embodiment, however, it is physically distinct device in communication with the management system 102. In an embodiment, the staging and processing module 110 is accessible through different security measures—such as a login and password—than are known to general users 108 and preferably only given to protocol designers 114. The staging and publishing module 110 can accept new protocol definitions. In an embodiment, the new protocol definitions are contained in xml files defining data elements and metadata, and the staging and publishing module 110 compares amended protocol's 116 to previous protocol's 112. In addition, in an embodiment, the staging and publishing module accesses a clinical database 104 to add new protocol data elements. In an embodiment, the staging and publishing module migrates patients from one protocol 112 to another protocol 116.

Network Interface Module

The management system 102 can also include a network interface module (not shown) that facilitates communication between the management system 102 and user's 108 remote systems via the communications network(s) 106. Additionally, a network interface module may be utilized for communication with a designer's 114 system.

The network interface module can utilize a variety of network protocols. In an embodiment, the network interface module includes the Hypertext Transfer Protocol (HTTP). However, it is to be appreciated from the present disclosure that other types of network communication protocols can be used. For example, the network interface module can utilize TCP/IP, FTP, HTTP, HTTPS, or any of a number of other suitable protocols. The network interface module may include a modem, Ethernet (NIC) card, wireless modem, cable modem, or other suitable interface.

Input and Output Devices

The management system 102 can communicate with a set of input and output devices. For example, the input device(s) can include a keyboard, roller ball, pen and stylus, mouse, trackball, voice recognition system, pre-designated switches or buttons, or other suitable devices. The input device(s) can also include a touch screen associated with an output device. Textual or graphic information can be entered through the input device. The output device(s) can include a speaker, display screen, printer, voice synthesizer, or other suitable device. In an embodiment, a designer 114 utilizes the management system directly.

Details

In an embodiment, management system 102 includes a conventional general purpose single-chip or multi-chip microprocessor such as, for example, a Pentium® processor, a Pentium® II processor, Pentium® III processor, Pentium® IV processor, a Pentium® Pro processor, an Intel Core Duo, an Intel Core 2 Duo, an xx86 processor, an 8051 processor, a MIPS® processor, a Power PC® processor, an ALPHA® processor, or other suitable personal computer or general purpose microprocessor. In addition, the microprocessor may be any special purpose microprocessor such as, for example, a digital signal processor, FPGA, ASIC, or other suitable special purpose microprocessor. Furthermore, the management systems 102 can each be used in connection with various operating systems such as: Microsoft® Windows® 3.X, Microsoft® Windows 95, Microsoft® Windows 98, Microsoft® Windows® NT, Microsoft® XP, Microsoft® Windows® CE, Palm Pilot OS, OS/2, Apple® MacOS®, Apple® OS X™, Disk Operating System (DOS), UNIX, Linux®, VxWorks, or IBM® OS/2®, Sun OS, Solaris OS, IRIX OS operating systems, or other operating systems.

In an embodiment, the management system 102 includes a server, a personal computer, a laptop computer, a portable computing device, a computer workstation, a local area network of individual computers, an interactive kiosk, a personal digital assistant, an interactive wireless communications device, a handheld computer, an embedded computing device, or other suitable computing device.

As can be appreciated by one of ordinary skill in the art from the disclosure herein, the management system 102 can include various sub-routines, procedures, definitional statements, and macros. The foregoing modules can be separately compiled and linked into a single executable program. However, it is to be appreciated by one of ordinary skill in the art from the disclosure herein that the processes performed by selected modules may be redistributed to other modules, combined together in a single module, made available in a shareable dynamic link library, or partitioned in any other logical way.

As used herein, the word module refers to logic embodied in hardware or firmware, or to a collection of software instructions, possibly having entry and exit points. Furthermore, the modules can be written in any programming language such as, for example, VB.NET, C, C++, C#, BASIC, Pascal, Java, FORTRAN, or other suitable language. The modules can be compiled and linked into an executable program, installed in a dynamic link library, or can be written in an interpreted programming language such as BASIC, Perl, or Python. Software modules can be callable from other modules or from themselves, and/or can be invoked in response to detected events or interrupts. Software instructions can be embedded in firmware and stored in a device, such as, for example, an EPROM, flash, or other suitable device. Hardware modules can be comprised of connected logic units, such as gates and flip-flops, and/or may be comprised of programmable units, such as programmable gate arrays or processors. The modules described herein are preferably implemented as software modules, but can be implemented in hardware or firmware.

User's 108 Systems/Designer 114's Devices

In an embodiment, the management system 102 provides remote access to users 108 and designers 114 having their own devices connected to a communications medium 106, such as the Internet. In an embodiment, a suitable device for accessing management system 102 is a PC comprising at least one each of input and output devices as well as a network interface module for communications with the management system 102 over communications medium 106. In an embodiment, one or more users and/or designers access the management system 102 directly, lessening or eliminating the need for separate devices.

In an embodiment, a user 108 electronically sends and receives data from the management system 102, via a browser module (not pictured). Such a user 108 device can send and receive data using one of any number of network protocols. In an embodiment, the request comprises a Hypertext Transfer Protocol (HTTP) request. However, it is to be appreciated from the disclosure herein that other types of network communication protocols can be used.

Browser Module

In an embodiment, a user's system 108 includes a browser module (not shown). For example, the browser module may present information to the user such as clinical trial data, patient information and registration forms, data submission forms, or other suitable information. The browser module and/or a web page accessible via the browser module can allow the user to request additional data, add data, delete data, and/or modify data for the clinical trial.

The browser module can be implemented as a module that uses text, graphics, audio, video, and/or other media to present data and to allow interaction with the data via the communications network. The browser module can be implemented as a combination of an all points addressable display such as a cathode-ray tube (CRT), a liquid crystal display (LCD), a plasma display, or other types and/or combinations of displays. In addition, the browser module can be implemented to communicate with input devices and may also include software with the appropriate interfaces which allow a user to access data through the use of stylized screen elements such as, for example, menus, windows, dialog boxes, toolbars, and controls (e.g., radio buttons, check boxes, sliding scales, etc.). Furthermore, the browser module communicates with a set of input and output devices to receive signals from the user.

Network Interface Module

The user's 108 and/or designer's 114 devices can also include a network interface module (not shown) that communicates with the management system 102 via the communications network.

The network interface module can utilize a variety of network protocols. In an embodiment, the network interface module includes the Hypertext Transfer Protocol (HTTP). However, other types of network communication protocols can be used. For example, the network interface module can utilize TCP/IP, FTP, HTTP, HTTPS, or other suitable protocols. The network interface module may include a modem, Ethernet (NIC) card, wireless modem, cable modem, or other suitable interface.

Input and Output Devices

In an embodiment, the user's 108 and/or designer's 114 devices communicate with a set of input and output devices. The input device(s) can include, for example, a keyboard, roller ball, pen and stylus, mouse, trackball, voice recognition system, pre-designated switches or buttons, or other suitable devices. The input device(s) can also include a touch screen associated with an output device. Textual or graphic information can be entered by the user through the input device. The output device(s) can include, for example, a speaker, a display screen, a printer, a voice synthesizer, or other suitable device.

Details

In an embodiment, the user's 108 and/or designer's 114 devices include a conventional general purpose single-chip or multi-chip microprocessor such as, for example, a Pentium® processor, a Pentium® II processor, Pentium® III processor, Pentium® IV processor, a Pentium® Pro processor, an Intel Core Duo, an Intel Core 2 Duo, an xx86 processor, an 8051 processor, a MIPS® processor, a Power PC® processor, an ALPHA® processor, or other suitable personal computer or general purpose microprocessor. In addition, the microprocessor can be any special purpose microprocessor such as, for example, a digital signal processor, FPGA, ASIC, or other suitable special purpose microprocessor. Furthermore, the user's 108 and/or designer's 114 devices may each be used in connection with various operating systems such as: Microsoft® Windows® 3.X, Microsoft® Windows 95, Microsoft® Windows 98, Microsoft® Windows® NT, Microsoft® XP, Microsoft® Windows® CE, Palm Pilot OS, OS/2, Apple® MacOS®, Apple® OS X™, Disk Operating System (DOS), UNIX, Linux®, VxWorks, or IBM® OS/2®, Sun OS, Solaris OS, IRIX OS operating systems, or other operating systems.

In an embodiment, the user's 108 and/or designer's 114 devices are personal computers, laptop computers, Blackberry® devices, portable computing devices servers, computer workstations, local area networks of individual computers, interactive kiosks, personal digital assistants, interactive wireless communications devices, handheld computers, embedded computing devices, or other suitable computing devices.

As can be appreciated by one of ordinary skill in the art from the present disclosure, a user or designer device can include various sub-routines, procedures, definitional statements, and macros. The foregoing modules can be separately compiled and linked into a single executable program. However, the processes that performed by selected modules can be redistributed other modules, combined together in a single module, made available in a shareable dynamic link library, or partitioned in any other logical way.

As used herein, the word module refers to logic embodied in hardware or firmware, or to a collection of software instructions, possibly having entry and exit points. Furthermore, the modules can be written in any programming language such as VB.NET, C, C++, C#, BASIC, Pascal, Java, FORTRAN, or other suitable language. The modules can be compiled and linked into an executable program, installed in a dynamic link library, or can be written in an interpreted programming language such as BASIC, Perl, or Python. It will be appreciated from the disclosure herein that software modules can be callable from other modules or from themselves, and/or can be invoked in response to detected events or interrupts. Software instructions may be embedded in firmware and stored in a device, such as, for example, an EPROM, flash, or other suitable device. Hardware modules can be comprised of connected logic units, such as gates and flip-flops, and/or may be comprised of programmable units, such as programmable gate arrays or processors. The modules described herein are preferably implemented as software modules, but can be implemented in hardware or firmware.

Alternatives

Although the foregoing has been described in terms of certain preferred embodiments, other embodiments will be apparent to those of ordinary skill in the art from the disclosure herein. Moreover, the described embodiments have been presented by way of example only, and are not intended to limit the scope of the disclosure. Indeed, the novel methods and systems described herein may be embodied in a variety of other forms without departing from the spirit thereof. Accordingly, other combinations, omissions, substitutions and modifications will be apparent to the skilled artisan in view of the disclosure herein. Thus, the present disclosure is not limited by the preferred embodiments, but is defined by reference to the appended claims. The accompanying claims and their equivalents are intended to cover forms or modifications as would fall within the scope and spirit of the disclosure.

What is claimed is:

1. A clinical trial management system comprising:
   a central processor for accepting clinical trial data comprising first clinical trial data and second clinical trial data;
   at least one database for storing the clinical trial data;

at least one set of metadata defining a first version of a protocol for a single clinical trial, wherein the central processor uses the at least one set of metadata to manage at least some of the clinical trial data; and a staging and publishing module for accepting an additional set of metadata defining a second version of the protocol for the single clinical trial, wherein:

the staging and publishing module adds data elements associated with the additional set of metadata to the at least one database, and the central processor concurrently manages the first clinical trial data for the single clinical trial according to at least one set of metadata of the at least one set of metadata defining the first version of the protocol and the second clinical trial data for the single clinical trial according to the additional set of metadata defining the second version of the protocol.

2. The clinical trial management system of claim 1, wherein:

the staging and publishing module comprises software instructions executed on the central processor.

3. The clinical trial management system of claim 2, wherein the staging and publishing module is capable of comparing the at least one set of metadata defining the first version of the protocol to the additional set of metadata defining the second version of the protocol and generating a report defining differences between the first version and the second version.

4. A method of concurrently managing multiple versions of a clinical trial protocol for a single clinical trial, the steps of the method comprising:

storing a first metadata file defining a first version of the protocol for the single clinical trial, wherein the first version defines at least one clinical data element to be stored in a database;

accepting at least one data element for storage as defined by the first metadata file;

accepting a second metadata file defining a second version of the protocol for the single clinical trial;

updating the database to store at least one clinical data element according to the second version;

tracking an association of each patient of a set of patients in the single clinical trial with the first or second version of the protocol;

determining whether a first patient of the set of patients is associated with the first or second version of the protocol; and storing data regarding the first patient of the set of patients according to the first version or the second version according to the association tracked for the first patient.

5. The method of claim 4, wherein the step of updating the database maintains all of the at least one clinical data element definitions of the first version.

6. The clinical trial management system of claim 1, wherein the added data elements comprise data collected for patients.

7. The clinical trial management system of claim 1, wherein the central processor concurrently manages the accepted clinical trial data for the single clinical trial by:

determining at least one patient associated with the accepted clinical trial data; and instructing the at least one database to store the accepted clinical trial data based, at least in part, on whether the at least one patient is associated with the first version or the second version of the protocol.

8. A method of staging a second version of a clinical trial protocol in a single clinical trial associated with a first version of the clinical trial protocol for the single clinical trial, the steps of the method comprising:

retrieving a first metadata file defining the first version of the protocol for the single clinical trial;

accepting a second metadata file defining the second version of the protocol for the single clinical trial;

comparing the first metadata file to the second metadata file; and generating a report of differences between the first and second metadata files.

9. A method of migrating patient records from a first version of a clinical trial protocol to a second version of the protocol for a single clinical trial, wherein a patient record includes at least one data store having at least one original data element and at least one metadata table defining the at least one data store and having at least one reference to the at least one data store, the steps of the method comprising:

adding a new data element to the at least one data store as required by the second version;

updating the at least one metadata table as required by the second version;

running, in response to updating the at least one metadata table, queries and derivations as required by the second version;

wherein the steps of adding, updating, and running preserve the at least one original data element in the at least one data store.

10. The method of migrating patient records of claim 9, wherein the step of updating the at least one metadata table includes adding an additional reference to the data store.

11. The method of migrating patient records of claim 9, wherein the step of updating the at least one metadata table includes changing the at least one reference to refer to the new data element.

12. The method of migrating patient records of claim 9, wherein the at least one metadata table comprises definitional entries and reference entries referring to the at least one data store's at least one data element; and the step of updating the at least one metadata table preserves definitional entries.

13. The method of migrating patient records of claim 9, wherein the at least one reference to the at least one data store comprises a pointer.

* * * * *